United States Patent
Kim et al.

(10) Patent No.: US 11,154,542 B2
(45) Date of Patent: Oct. 26, 2021

(54) NAIL LACQUER COMPOSITION CONTAINING CICLOPIROX

(71) Applicant: GENUONE SCIENCES INC., Seoul (KR)

(72) Inventors: Nam-hyang Kim, Chungcheongnam-do (KR); Yong-baik Cho, Gyeonggi-do (KR); Sang-young Jeong, Daejeon (KR); Byoung-chan Bae, Sejong-si (KR); Jae-seong Lee, Gyeonggi-do (KR); Ji-won Lee, Sejong-si (KR); Hong-koo Cho, Seoul (KR)

(73) Assignee: GENUONE SCIENCES INC., Seoul (KR)

( * ) Notice: Subject to any disclaimer, the term of this patent is extended or adjusted under 35 U.S.C. 154(b) by 0 days.

(21) Appl. No.: 15/555,619

(22) PCT Filed: Mar. 9, 2016

(86) PCT No.: PCT/KR2016/002333
§ 371 (c)(1),
(2) Date: Sep. 5, 2017

(87) PCT Pub. No.: WO2016/159532
PCT Pub. Date: Oct. 6, 2016

(65) Prior Publication Data
US 2018/0104227 A1    Apr. 19, 2018

(30) Foreign Application Priority Data
Mar. 28, 2015    (KR) ........................ 10-2015-0043724

(51) Int. Cl.
| | | |
|---|---|---|
| *A61K 31/4412* | (2006.01) | |
| *A61Q 17/00* | (2006.01) | |
| *A61Q 3/02* | (2006.01) | |
| *A61K 8/81* | (2006.01) | |
| *A61K 8/49* | (2006.01) | |
| *A61K 31/4418* | (2006.01) | |
| *A61K 47/22* | (2006.01) | |
| *A61K 47/10* | (2017.01) | |
| *A61K 9/00* | (2006.01) | |
| *A61K 47/18* | (2017.01) | |
| *A61P 31/10* | (2006.01) | |
| *A61K 9/70* | (2006.01) | |
| *A61K 47/32* | (2006.01) | |
| *A61K 47/38* | (2006.01) | |

(52) U.S. Cl.
CPC ........ *A61K 31/4412* (2013.01); *A61K 8/4926* (2013.01); *A61K 8/8152* (2013.01); *A61K 8/8158* (2013.01); *A61K 9/0014* (2013.01); *A61K 9/7015* (2013.01); *A61K 31/4418* (2013.01); *A61K 47/10* (2013.01); *A61K 47/18* (2013.01); *A61K 47/22* (2013.01); *A61K 47/32* (2013.01); *A61K 47/38* (2013.01); *A61P 31/10* (2018.01); *A61Q 3/02* (2013.01); *A61Q 17/005* (2013.01)

(58) Field of Classification Search
None
See application file for complete search history.

(56) References Cited

U.S. PATENT DOCUMENTS

| | | | | |
|---|---|---|---|---|
| 6,224,887 B1 * | 5/2001 | Samour | ................ | A61K 8/4926 424/401 |
| 8,697,753 B1 * | 4/2014 | Mailland | .............. | A61K 9/0014 514/655 |

FOREIGN PATENT DOCUMENTS

| | | | | |
|---|---|---|---|---|
| JP | 2001-523273 | 11/2001 | ............. | A61K 7/043 |
| JP | 2005-503318 | 2/2005 | ............. | A61K 45/00 |
| KR | 10-2003-0016237 | 2/2003 | ......... | A61K 31/4196 |
| KR | 10-0551930 | 2/2006 | ............. | A61K 47/32 |
| WO | WO 2002/07683 | * 1/2002 | ............. | A61K 7/043 |
| WO | WO 2006-013963 | 2/2006 | ............. | A61K 47/32 |

OTHER PUBLICATIONS

International Search Report from corresponding PCT Application No. PCT/KR2016/002333 dated Sep. 5, 2016 and its English translation.

* cited by examiner

*Primary Examiner* — Craig D Ricci
(74) *Attorney, Agent, or Firm* — Harness, Dickey & Pierce, P.L.C.

(57) ABSTRACT

The present invention relates to a nail lacquer composition containing at least one antifungal agent as a pharmacologically active ingredient. The present invention has an excellent penetrating effect of a drug in skin areas where the drug is applied because of needing treatment and, specifically, in fingernails by containing a polymer material which forms a specific film, and a penetration enhance, is convenient for management after locally applying the drug to a treatment site, and has excellent storage stability of the drug.

7 Claims, 2 Drawing Sheets

NAIL LACQUER COMPOSITION CONTAINING CICLOPIROX

CROSS-REFERENCE TO RELATED APPLICATIONS

This application is a national phase application of PCT Application No. PCT/KR2016/002333, filed on Mar. 9, 2016, which claims the benefit and priority to Korean Patent Application No. 10-2015-0043724 filed on Mar. 28, 2015. The entire disclosures of the applications identified in this paragraph are incorporated herein by references.

TECHNICAL FIELD

The present invention relates to a nail lacquer composition containing at least one antifungal agent as a pharmacologically active ingredient.

BACKGROUND

[Mycosis]

The present invention relates to a nail lacquer composition useful for the prevention or treatment of mycosis, specifically dermatomycosis, more specifically onychomycosis.

Onychomycosis, which is progressive or recurrent fungal infection, refers to all injections caused by fungus including dermatophyte and yeast fungus. This disease is characterized in that in general, injections caused by this disease start from the nail bed and progresses to the nail plate. Onychomycosis is superficial, but this may cause a significant health problem to oneself or other persons. Thus, it is necessary to deal with this disease carefully.

Firstly, in a person infected with fungus, a fungal reservoir is made on the primary infection site, and the fungus can be propagated to a second other site of the body of the person through a direct or indirect contact with the reservoir, and furthermore, the fungus can infect other persons who have sensitivity.

Secondly, onychomycosis increases the sensitivity of a patient to other serious diseases. For example, onychomycosis increases the likelihood of onset of diseases such as recurrent cellulites or thrombophlebitis, etc., and onychomycosis promotes the exposure of the secondary bacterial infection, particularly, in a patent with diabetes, which causes foot ulcers or gangrene, etc.

Thirdly, apart from such serious diseases, onychomycosis had great social and psychological influences on patients. According to the recent study results, 92% of patients with onychomycosis think that they have psychosocially and physically negative influences due to this disease, and 67 to 74% of the patients feel embarrassed due to athlete's foot on the nail caused by this disease. In addition, 36 to 48% of the patients feel a pain due to this disease, and 41% of the patients have a restriction of behavior due to this disease. As such, onychomycosis exerts a bad influence on a self-image and self-respect, which results in a negative influence on the quality of life.

[Actual Condition on Treatment of Mycosis, Etc.]

Despite that onychomycosis is a disease that has great influences on the health of patients and the quality of life, some doctors refuse to treat this disease. The reason is because the initial onychomycosis which shows mild symptoms is considered as the problem of beauty, not the problem of health, or the doctors are rather concerned about side effects of systemic therapy during the treatment process, e.g. side effects of drugs for oral administration. For example, most of commercially available therapeutic agents for oral administration of onychomycosis are azole-based drugs, which have been known as exerting side effects such as gastrointestinal disturbance, etc. when the drugs are administered and absorbed into the whole body.

For this reason, there have been continuous needs on therapeutic agents for topical application, which have less side effects, by directly applying the agents only onto a desired site which needs treatment, not a systemic therapy such as a drug for oral administration, while at the same time, obtaining a satisfactory effect with a self-treatment without visiting a hospital.

[Examples of Existing Therapeutic Agents for Topical Application]

Representative examples of drugs that have an antifungal activity include Amorolfine (Phenyl-morpholine derivatives), Ciclopirox, Hydroxypiridone, etc.

Amorolfine has an antifungal activity by inhibiting the synthesis of ergosterol of a fungal cell membrane, and this is the active ingredient of commercially available products such as Loceryl™ (GALDERMA, France). Flagothier. etc. have discovered through the laboratory researches that amorolfine has a low antifungal activity but is effective in reducing the formation of spores that resists against antifungal agents, thereby lowering the risk of reinfection.

Ciclopirox acts on a trivalent cation-dependent enzyme, unlike the mechanism of azol or other antifungal drugs, and inhibits the migration of essential substances or ions in cell through a fungal membrane, thereby exerting an antifungal activity, and also exerting an anti-inflammatory activity in addition to the antifungal activity. This is an active ingredient of commercially available products such as Loprox™ (Höchst, Germany), etc.

Other than the above, Tioconazole, Miconazole, Salicylic acid and Undecenoates, etc. have been used as topical therapeutic agents for onychomycosis.

[Restriction of Existing Therapeutic Agents for Topical Application]

Onychomycosis is a disease generally caused by fungus that is penetrated into inside of the nail, i.e. the surface of the nail facing to dead skin layers (nail bed), proliferated with keratin constituting the nail, and spread to the outside of the nail (nail plate). In order to treat this disease, when a drug is applied onto the outside (nail plate), the drug should reach the inside (nail bed) that needs the treatment; however, it is not easy to allow a drug to be penetrated into the nail, unlike the skin. Consequently, since tropical antifungal agents in the form of general cream or ointment are difficult to be penetrated into the hard nail plate, the targeted therapeutic effect cannot be achieved by using the agents in the same manner as drugs that are applied on the skin.

Thus, at an initial stage, a sealing therapy of keratolytic and an antifungal agent using chemicals was used, or in the case of Loceryl™, the method of grinding the nail plate and subsequently applying the drug was used.

Thereafter, recently, Lacquer products with enhanced penetration of a drug have been developed. As one example of the products, there is Fenrakk™ containing ciclopirox, wherein ethyl acetate and isopropyl alcohol are used as solvents, and a polymer [Methylvinyl ether/maleic acid] of butyl monoester is used as a film-forming substrate.

DETAILED DESCRIPTION OF INVENTION

Technical Task

A Lacquer product is a special therapeutic agent for a localized region, focusing on the characteristic of the nail into which a drug is difficult to be penetrated as compared to skin tissues. This product is characterized by forming a constant membrane on a drug to prevent the disappearance of the drug such that the drug can continuously be penetrated into inside of the nail without disappearing or deforming the drug on the region to be applied, because the drug takes a long time to be penetrated into the targeted region. Consequently, in order to understand Lacquer products, it is necessary to first figure out the characteristic of the membrane.

The commercially available medicine, Fenrakk™, is characterized by treating the nail with a drug solution using an insoluble film. On the other hand, in the case of Lacquer products, when it is to apply the drug after a certain period, the penetration of the drug is easy only when the film is removed. However, the insoluble film is not easy to be removed if the insoluble film is not an organic solvent, etc. In other words, Fenrakk™ has a problem that the compliance with a patient is low, and the transmittance of the drug is also not satisfactory.

Korean Patent No. 10-0530263, which relates to a product that overcomes the dermatological and esthetical drawback of existing nail lacquers such as Fenrakk™ presents an antimicotic local composition containing at least one antimycotic agent and derivatives of chitosan, which is one kind of a water soluble film forming agent, not an insoluble film. However, this composition also has an unsatisfactory penetrating effect of a drug. Particularly, the composition has the restriction that since the drug can be immediately washed when it is in a contact with a small amount of water after applying the drug, the sufficient amount of the drug should remain in the environment where there is absolutely no water on the region where the drug is applied, for a certain period, e.g. more than 6 hours, for allowing the drug to reach the region that needs treatment, which causes inconvenience for use in view of patients.

Meanwhile, Korean Patent Laid-Open No. 10-2014-0124404 presents antifungal local compositions wherein dimethylsulfoxide (DMSO) is used as a solvent, in order to enhance a penetrating effect of a drug. However, DMSO is a substance that causes skin stimulation and inflammation, and thus this is not preferable.

The present invention has the task to overcome the drawbacks of the above prior art technologies, and is has an excellent penetrating effect of a drug in skin areas and convenient for of use in view of patients.

Means for Achieving Task

The present invention achieved the above task with the following means:

(1) A composition containing at least one antifungal agent and at least one film forming agent, characterized in that the film forming agent is at least one selected from the group consisting of an octylacrylamide acrylate copolymer, an acrylic acrylate copolymer, a styrene acrylate copolymer, an aminoalkyl methacrylate copolymer, an acrylate methacrylate copolymer, an ammonio methacrylate copolymer, an acrylate ammonium methacrylate copolymer, an acrylate dimethylaminoethyl methacrylate copolymer, and octylacrylamide acrylate butylaminoethyl methacrylate copolymer.

(2) The composition according to (1) above, characterized by further containing at least one selected from the group consisting of hydroxypropylmethylcellulose and hydroxypropylmethylcellulose.

(3) The composition according to (1) or (2) above, characterized by further containing at least one selected from the group consisting of urea, cetostearyl alcohol, campa and N-methyl-2-pyrrolidone.

(4) The composition according to any one of (1) to (3) above, characterized in that the antifungal agent is ciclopirox or a pharmaceutically acceptable salt thereof.

(5) The composition according to any one (1) to (4) above, characterized in that the amount of ciclopirox or a pharmaceutically acceptable salt thereof is 0.001-30 wt. %, in particular, preferably, 0.5-10 wt. %, relative to the total weight of the composition.

(6) The composition according to any one of (1) to (5) above, characterized in that the amount of the film forming agent is 0.5-30 wt %, in particular, preferably, 1.0-15 wt. %, relative to the total weight of the composition.

(7) The composition according to any one of (1) to (6) above, characterized in that the amount of at least one selected from the group consisting of hydroxypropylmethylcellulose and hydroxypropylmethylcellulose is 0.001-10 wt. %, relative to the total weight of the composition.

(8) The composition according to any one of (1) to (7) above, characterized in that the amount of at least one selected from the group consisting of urea, cetostearyl alcohol, campa and N-methyl-2-pyrrolidone is 0.01-10 wt. %, relative to the total weight of the composition.

Effect of Invention

The present invention has the effects that the invention has an excellent penetrating effect of an antifungal drug into the nail, has no inconvenience in removing a film formed when applying the drug solution primarily and then applying a drug solution secondarily after a certain period, the drug applied is not easily washed with a small amount of water.

BEST MODE FOR EMBODIMENT OF INVENTION

Figure 1:
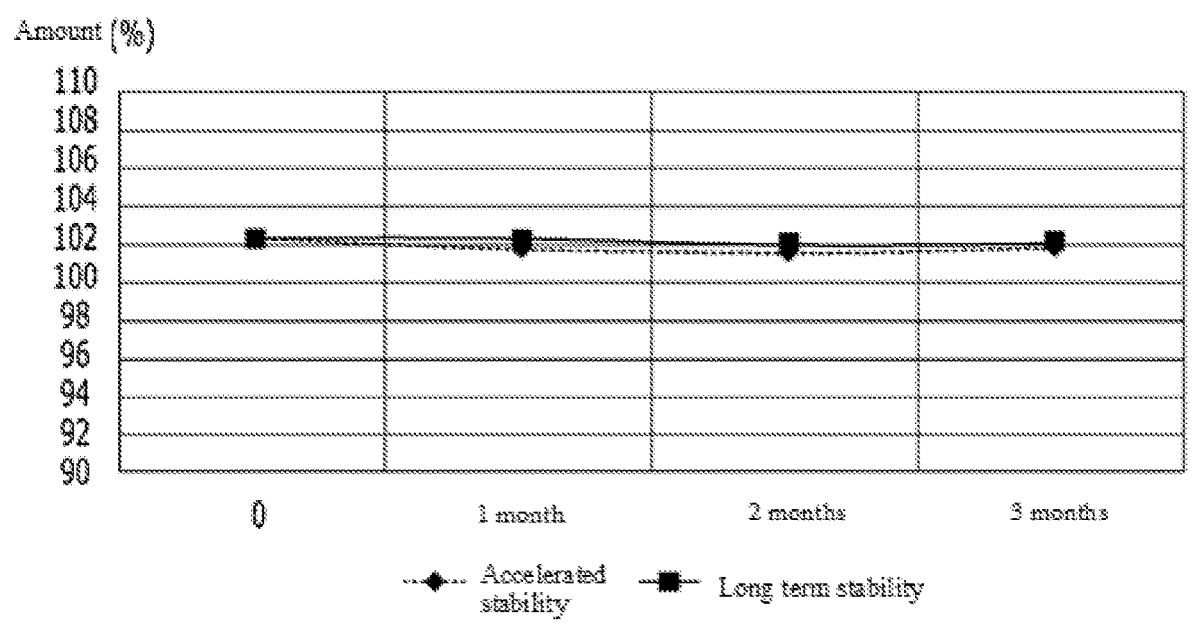
FIG. 1 shows the comparison results of the amounts of the active ingredients remaining inside of toenail during the period after applying the test drug and the control drug.

The present invention relates to a nail lacquer composition containing an antifungal agent as an active ingredient, wherein the composition contains an active ingredient, a specific film forming agent, a solvent and other additives, etc.

[Antifungal Agent]

The present invention contains at least one antifungal agent. The antifungal agent can be selected from any known antifungal agents of synthetic or natural origin. In addition, the active agent can be in the free form, and can also be in the form of free acid, free base or other salts.

The examples of the known antifungal agents include, but are not limited to, 1-hydroxy-2-pyridone compounds, e.g., ciclopirox, rilopirox, piroctone, ciclopirox olamine or the compound disclosed U.S. Pat. No. 4,957,730; imidazole derivatives, e.g., clotrimazole, econazole, isoconazole, ketoconazole, miconazole, thioconazole, bifonazole, fenticonazole or oxiconazole; polyene derivatives, e.g., nystatin, natamycin or amphotericin; allylamine derivatives, e.g., niphtipine or terbinapine; triazole derivatives, e.g., fluconazole, itraconazole, terconazole or voriconazole; morpholine derivatives, e.g., amorolfine or the compound disclosed in U.S. Pat. No. 5,120,530; griseofulvin; acidic compounds, e.g. undecylenic acid; tolnaftate; or flucytosine, etc.

In addition, as known antifungal agents, there is natural origin, in particular, plant extracts, for example, leaf extracts of tea-tree oil, lavender oil or neem tree, etc.

The present invention can use the known antifungal agent alone or a mixture of two or more different antifungal agents. In particular, if the antifungal agent is of natural origin, the use of the mixture of two or more different antifungal agents is more preferable in the expression of the drug efficacy.

In the aspect of the expression of the other effect as well as the expression of the drug efficacy, when using the antifungal agent alone or blending two or more different components, it is the most preferable to select ciclopirox basically. The amount of the antifungal agent may vary depending on structure, antimicrobial activity, release speed from nail lacquer film, spreading property and penetration into the nail, and this can be properly selected by a person skilled in the art. However, when containing ciclopirox as the antifungal agent, it is preferable to select ciclopirox in the amount of 0.001-30 wt. % relative to the total amount of the composition, and in particular, in the aspect of the expression of the targeted effect, it is the most preferable to select ciclopirox in the amount of 0.5-10 wt. %.

[Film Forming Agent]

The present invention contains at least one film forming agent. The film forming agent refers to a component of a binder essential to form a film such as a thin membrane or cover.

There are several components as film forming agents known in this art. As aforementioned, in the commercially available medicine, Fenrakk™, an insoluble film forming agent was selected, and in Korean Patent No. 10-0530263, derivatives of chitosan, which are one kind of a water soluble film forming agent, were selected. However, the present inventors believed that the insoluble film forming agent has an excellent waterproof, but has a disadvantage that the formed film should be removed when applying the drug secondarily after applying the drug primarily to have a good penetrating power of the drug, but in order to remove the formed film, the use of an organic solvent, etc. is required, so the process is very inconvenient, and that the chitosan derivatives have a disadvantage that they are sensitive to the water, when applying the drug, the drug generally needs about 6 hours to be penetrated into the shell to sufficiently reach to a site to be treated, but the drug can be cleansed by being in contact with a small amount of water. Most of all, the film forming agent has unsatisfactory penetration of a drug into the nail.

However, surprisingly, the present inventors have found that when selecting, as a film forming agent, at least one selected from the group consisting of an octylacrylamide acrylate copolymer, an acrylic acrylate copolymer, a styrene acrylate copolymer, an aminoalkyl methacrylate copolymer, an acrylate methacrylate copolymer, an ammonio methacrylate copolymer, an acrylate ammonium methacrylate copolymer, an acrylate dimethylaminoethyl methacrylate copolymer, and octylacrylamide acrylate butylaminoethyl methacrylate copolymer, the above disadvantages were all overcome, and discovered that the treatment of the disease has a surprising synergistic effect with an antifungal agent, in particular, ciclopirox, in the aspect of the targeted effect, and then the inventors completed the present invention.

The film forming agent according to the present invention is a type that when applying the agent onto the nail together with a solvent, while the solvent is evaporated, a film is formed on the nail and maintained until it exposes to traditional typical hygienic cleaning cycles and then removed. This film forming agent is strong and flexible, has good waterproof, excellent in the easiness of cleaning, and most of all, can improve the penetration of a drug into the nail.

The film forming agent is preferably selected in the amount of 0.5-30 wt. %, relative to the total amount of the composition, and in particular, most preferably, selected in the amount of 1.0-15 wt. % in the aspect to the expression of the targeted effect.

[Solvent]

The present invention contains at least one physiologically acceptable solvent. As solvents, ethanol, isopropanol, ethyl acetate, butyl acetate, acetone or a mixture thereof, which are organic solvents that are physiologically acceptable and compatible with other components, including the drug and the film forming agent, of the composition, are preferred.

Herein, the organic solvent is present in the composition in the amount sufficient to dissolve the components to be liquefied, e.g. a solid component, the film forming agent and other additives, and the organic solvent can be used in the amount of 40-90 wt. %, more preferably, 60-85 wt. %, relative to the total weight of the composition. In addition, as a solvent, water can be used because the penetration of the drug into hydration of the nail is easy and for the reduction of stimulus due to frequent and repeated exposures of the organic solvent to the nail and adjacent skin. Here, water can be used in the amount of 0-20 wt. %, preferably, 1-10 wt. %, relative to the total weight of the composition. However, in this case, it should be noted that the amount should be selected in the range that does not affect the problems of long term stability due to the degradation of the compatibility with other solvents and components, for example, phase separation, precipitation or the degradation of the content of the active component.

[Other Additives]

The present invention can further contain at least one ingredient selected from the group consisting of polyvinylpyrrolidone, vinylpyrrolidone-vinylacetate copolymer, hydroxyalkyl cellulose and alkylcellulose, in order to improve the hydrophilic property of the film membrane.

In addition, the present invention can further contain at least one ingredient selected from the group consisting of N-methyl-2-pyrrolidone, cetostearyl alcohol, cetanol, stearyl alcohol, urea, campa and salicylic acid, in order to improve nail penetration of the composition.

Depending on cases, the present invention can contain antibiotic, anti-inflammatory agents, preservatives and/or local anesthetics, and can also contain other existing additives typically blended in nail lacquer for cosmetics or treatment, e.g., precipitation retarder, chelating agent, antioxidant, silicate, aroma component, wetting agent, lanolin derivatives, optical stabilizer or antibacterial component.

[Preparation Method]

The present invention can be prepared according to the general method typically used for the preparation of nail lacquers. For example, the present invention can be prepared by adding at least one antifungal agent, at least one film forming agent selected from the group consisting of an octylacrylamide acrylate copolymer, an aminoalkyl methacrylate copolymer and an alkyl acrylate methylmethacrylate copolymer, and other additives into a solvent or a mixture of solvents, respectively or simultaneously, and individually stirring the mixture with other liquid components simultaneously or by a typical mixing technique. Herein, there is no particular standard in the order of adding the individual components, and the order can be properly selected by a person skilled in the art. If any component is presented in the solid form, it is preferable to gradually add the ingredients into the liquid component in order to prevent clumping.

Hereinafter, the present invention will be explained in more detail through specific examples. Please note that the following examples are only to exemplify the present invention, and the scope of the present invention is not limited to the following examples.

FORM FOR EMBODIMENT OF THE INVENTION

Example 1

A nail lacquer composition was prepared by mixing the liquid components of Table 1 in a container provided with a stirrer, and then successively adding the components and stirring the mixture until the components were dissolved.

TABLE 1

| Component | Wt. % relative to the total amount of the composition |
|---|---|
| Ciclopirox | 8% |
| Octylacrylamide acrylate copolymer | 8% |
| Hydroxypropylcellulose | 0.2% |
| Ethanol | 62.3% |
| Ethyl acetate | 10% |
| Water | 10% |
| Urea | 0.5% |
| Setostearyle alcohol | 1% |

Figure 2:
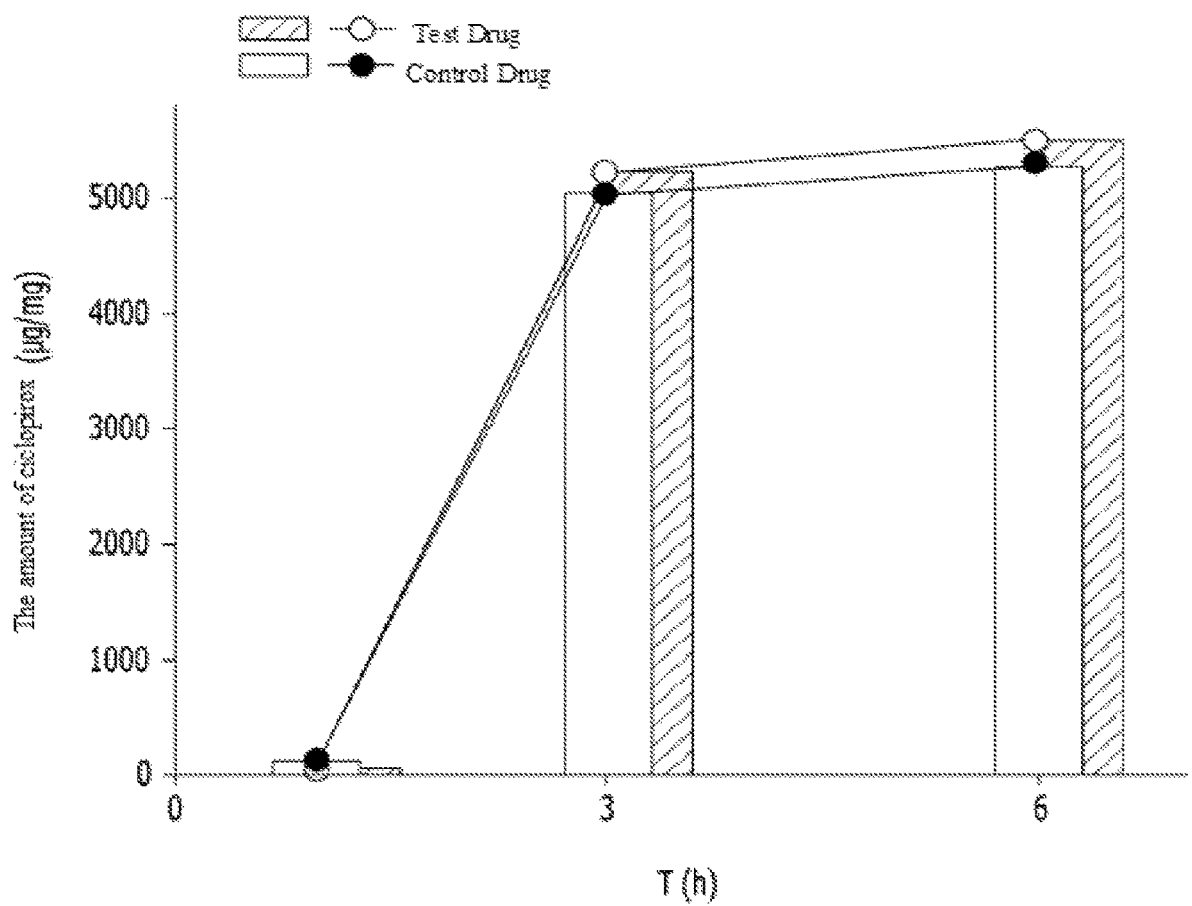
FIG. 2 shows the analysis results of the amounts of the active ingredients under the accelerated storage condition and the long storage condition of the test drug.

The present nail lacquer composition was transparent for a long period, maintained the uniform phase, and maintained the uniform film membrane without disappearing until it was exposed to the cleaning cycle, so the drug could have exerted the continuous efficacy. In addition, as will be explained in Experimental Examples 1 and 2, the present nail lacquer composition was also excellent in the nail penetration and storage stability as shown in FIGS. 1 and 2.

Example 2

The nail lacquer composition was prepared according to the same method as in Example 1 using the components of Table 2.

TABLE 2

| Component | Wt. % relative to the total amount of the composition |
|---|---|
| Ciclopirox | 8% |
| Octylacrylamide acrylate copolymer | 5% |
| Hydroxypropylcellulose | 0.3% |
| Ethanol | 65.2% |
| Ethyl acetate | 10% |
| Water | 10% |
| Urea | 0.5% |
| Setostearyle alcohol | 1% |

The present nail lacquer composition showed the phase and properties equivalent to the nail lacquer composition of Example 1.

Example 3

The nail lacquer composition was prepared according to the same method as in Example 1 using the components of Table 3.

TABLE 3

| Component | Wt. % relative to the total amount of the composition |
|---|---|
| Ciclopirox | 8% |
| Octylacrylamide acrylate copolymer | 5% |
| Hydroxypropylcellulose | 0.2% |
| Ethanol | 68.3% |
| Ethyl acetate | 15% |
| Water | 2% |
| Urea | 0.5% |
| Setostearyle alcohol | 1% |

The present nail lacquer composition showed the phase and properties equivalent to the nail lacquer composition of Example 1.

Example 4

The nail lacquer composition was prepared according to the same method as in Example 1 using the components of Table 4.

TABLE 4

| Component | Wt. % with respect to the total amount of the composition |
|---|---|
| Ciclopirox | 8% |
| Octylacrylamide acrylate copolymer | 8% |
| Hydroxypropylcellulose | 0.2% |
| Ethanol | 72.3% |
| Ethyl acetate | 5% |
| Water | 5% |
| Urea | 0.5% |
| Setostearyle alcohol | 1% |

The present nail lacquer composition showed the phase and properties equivalent to the nail lacquer composition of Example 1.

Example 5

The nail lacquer composition was prepared according to the same method as in Example 1 using the components of Table 5.

TABLE 5

| Component | Wt. % with respect to the total amount of the composition |
|---|---|
| Ciclopirox | 8% |
| Octylacrylamide acrylate copolymer | 8% |
| Hydroxypropylcellulose | 0.2% |
| Ethanol | 42.3% |
| Ethyl acetate | 20% |
| Water | 10% |
| Urea | 10% |
| Setostearyle alcohol | 0.5% |

The present nail lacquer composition showed the phase and properties equivalent to the nail lacquer composition of Example 1.

Example 6

The nail lacquer composition was prepared according to the same method as in Example 1 using the components of Table 6.

TABLE 6

| Component | Wt. % with respect to the total amount of the composition |
|---|---|
| Ciclopirox | 8% |
| Octylacrylamide acrylate copolymer | 8% |
| Hydroxypropylcellulose | 0.2% |
| Ethanol | 67.3% |
| Ethyl acetate | 10% |
| Water | 5% |
| Urea | 0.5% |
| Setostearyle alcohol | 1% |

The present nail lacquer composition showed the phase and properties equivalent to the nail lacquer composition of Example 1.

Example 7

The nail lacquer composition was prepared according to the same method as in Example 1 using the components of Table 7.

TABLE 7

| Component | Wt. % with respect to the total amount of the composition |
|---|---|
| Ciclopirox | 8% |
| Octylacrylamide acrylate copolymer | 8% |
| Hydroxypropylcellulose | 0.2% |
| Ethanol | 72.3% |
| Ethyl acetate | 5% |
| Water | 5% |
| Urea | 0.5% |
| Setostearyle alcohol | 1% |

The present nail lacquer composition showed the phase and properties equivalent to the nail lacquer composition of Example 1.

Example 8

The nail lacquer composition was prepared according to the same method as in Example 1 using the components of Table 8.

TABLE 8

| Component | Wt. % with respect to the total amount of the composition |
|---|---|
| Ciclopirox | 8% |
| Octylacrylamide acrylate copolymer | 8% |
| Hydroxypropylcellulose | 0.2% |
| Ethanol | 60.8% |
| Ethyl acetate | 10% |
| Water | 10% |
| Urea | 2% |
| Setostearyle alcohol | 1% |

The present nail lacquer composition showed the phase and properties equivalent to the nail lacquer composition of Example 1.

Example 9

The nail lacquer composition was prepared according to the same method as in Example 1 using the components of Table 9.

TABLE 9

| Component | Wt. % with respect to the total amount of the composition |
|---|---|
| Ciclopirox | 8% |
| Octylacrylamide acrylate copolymer | 8% |
| Hydroxypropylcellulose | 0.2% |
| Ethanol | 62.3% |
| Ethyl acetate | 15% |
| Water | 5% |
| Urea | 0.5% |
| Setostearyle alcohol | 1% |

The present nail lacquer composition showed the phase and properties equivalent to the nail lacquer composition of Example 1.

Example 10

The nail lacquer composition was prepared according to the same method as in Example 1 using the components of Table 10.

TABLE 10

| Component | Wt. % with respect to the total amount of the composition |
|---|---|
| Ciclopirox | 8% |
| Octylacrylamide acrylate copolymer | 8% |
| Hydroxypropylcellulose | 0.2% |
| Ethanol | 60.8% |
| Ethyl acetate | 15% |
| Water | 5% |
| Urea | 2% |
| Setostearyle alcohol | 1% |

The present nail lacquer composition showed the phase and properties equivalent to the nail lacquer composition of Example 1.

[Experimental Example 1] Test for Nail Penetration of Active Ingredient Using Pig Tonail The comparison test was conducted by selecting, as a test drug, the composition of Example 1, and selecting, as a control drug, the commercially available product (Full Care Nail Lacquer™) consisting of the mixed ingredients of the following Table 11.

TABLE 11

| Mixed ingredients |
|---|
| Ciclopirox |
| Ethyl acetate |
| Ethanol |
| Setostearyle alcohol |
| Hydroxypropyl Chitosan |
| Water |

Example 1 (Ciclopirox 80 mg among about 1 g), which is the test drug, and the commercially available product (Full Care Nail Lacquer™) containing the same amount (Ciclopirox 80 mg among about 1 g) of the active ingredient as Example 1, which is the control drug, were applied onto the pig toenail having a diameter of 1.5 cm, in the amount of 1 mL (about 80 mg as Ciclopirox), respectively. After the application for 1 hour, 3 hours and 6 hours, the toenail was made into thin fragments using Microtome, and 10 mL methanol was put and subjected to ultrasonication for 1 hour at 50°, and then measured according to the high pressure liquid chromatography. The results are shown in FIG. 1.

Upon comparing the total amount of the active ingredient penetrated into the toenail through FIG. 1, it can be figured out that the test drug showed relatively higher penetration as compared to the control drug, so the final penetration amount and the total penetration amount are similar or higher than those of the control drug. In other words, although the test drug has slightly lower waterproof property as compared to insoluble nail lacquers that use a large amount of pungent organic solvents, its waterproof property is not bad to the extent that the drug is disappeared when it is in a slight contact with water like the control drug, and the test drug can maintain the uniform film membrane until it is exposed to the hygienic cleaning cycles, and is excellent in the penetration of the active ingredient. Considering all of the above, the test drug is the most suitable antifungal nail lacquer as compared to prior art technologies known so far.

[Experimental Example 2] Stability Test of Active Ingredient

The amount of the active ingredient of the test drug in Experimental Example 1 was measured according to high pressure liquid chromatography, and then stored for 3 months under the accelerated storage condition (Temperature 40° C., Relative humidity 75%) and the long storage condition (Temperature 25° C., Relative humidity 60%). Thereafter, after 1 month, 2 months and 3 months, the amount of the active ingredient was measured again according to high pressure liquid chromatography. The results are shown in FIG. 2

It was confirmed that in the test drug, under the accelerated storage condition, even after the storage for 3 months, the amount of the active ingredient is maintained almost the same as that before the storage and that under the long storage condition.

In other words, in the test drug, the composition of the nail lacquer is maintained stably in the active ingredient exerting the efficacy as well as in appearance and thus the test drug is suitable as an antifungal nail lacquer.

What is claimed is:

1. A nail lacquer composition comprising at least one antifungal agent, at least one film forming agent, at least one solvent and water, wherein
    the at least one antifungal agent is ciclopirox or a pharmaceutically acceptable salt thereof;
    the film forming agent is an octylacrylamide acrylate copolymer in an amount of 0.5 to 15 wt % relative to the total weight of the composition;
    the at least one solvent is ethanol in an amount of 60 to 85 wt % relative to the total weight of the composition; and
    wherein the amount of water is 5 to 20 wt %, relative to the total weight of the composition.

2. The composition according to claim 1, further containing at least one selected from the group consisting of hydroxypropylmethylcellulose and hydroxypropylmethylcellulose.

3. The composition according to claim 1, further containing at least one selected from the group consisting of urea, cetostearyl alcohol, and N-methyl-2-pyrrolidone.

4. The composition according to claim 1, wherein the amount of ciclopirox or a pharmaceutically acceptable salt thereof is 0.5-10 wt. %, relative to the total weight of the composition.

5. The composition according to claim 2, wherein the amount of at least one selected from the group consisting of hydroxypropylmethylcellulose and hydroxypropylmethylcellulose is 0.001-10 wt. %, relative to the total weight of the composition.

6. The composition according to claim 3, wherein the amount of at least one selected from the group consisting of urea, cetostearyl alcohol, and N-methyl-2-pyrrolidone is 0.01-10 wt. %, relative to the total weight of the composition.

7. The composition according to claim 2, further containing at least one selected from the group consisting of urea, cetostearyl alcohol, and N-methyl-2-pyrrolidone.

* * * * *